(12) United States Patent
Mauro et al.

(10) Patent No.: US 7,745,686 B2
(45) Date of Patent: Jun. 29, 2010

(54) CATAMENIAL DEVICE

(75) Inventors: Anthony J. Mauro, Allenhurst, NJ (US); Mark E. Rosengarten, Suffern, NY (US); Irwin Butensky, Teaneck, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 10/003,915

(22) Filed: Nov. 2, 2001

(65) Prior Publication Data

US 2003/0100871 A1 May 29, 2003

(51) Int. Cl.
*A61F 13/20* (2006.01)
(52) U.S. Cl. .................. 604/360; 604/385.18; 604/904
(58) Field of Classification Search .................. 604/360, 604/904, 361, 385.18, 304, 359, 367; 602/48, 602/50, 51
See application file for complete search history.

(56) References Cited

U.S. PATENT DOCUMENTS

| | | | | |
|---|---|---|---|---|
| 4,357,476 A | * | 11/1982 | Reinchr et al. | 564/509 |
| 4,628,048 A | * | 12/1986 | Acker et al. | 514/63 |
| 4,818,594 A | * | 4/1989 | Albien et al. | 442/121 |
| 5,062,973 A | * | 11/1991 | Kellett | 510/519 |
| 5,705,182 A | | 1/1998 | Brown-Skrobot | 424/431 |
| 5,733,272 A | | 3/1998 | Brunner et al. | 604/359 |
| 5,753,252 A | | 5/1998 | Brown-Skrobot | 424/431 |
| H1732 H | | 6/1998 | Johnson | 428/68 |
| 5,783,502 A | * | 7/1998 | Swanson | 442/123 |
| 5,797,891 A | | 8/1998 | Wiersma | 604/360 |
| 5,817,047 A | | 10/1998 | Osborn, III et al. | 604/14 |
| 5,817,844 A | * | 10/1998 | Hama et al. | 554/149 |
| 5,840,794 A | * | 11/1998 | Borgman | 514/398 |
| 5,856,248 A | | 1/1999 | Weinberg | 442/118 |
| 5,859,077 A | | 1/1999 | Reichman et al. | 521/84.1 |
| 5,869,410 A | * | 2/1999 | Smith et al. | 442/333 |
| 5,873,868 A | | 2/1999 | Nakahata | 604/383 |
| 5,891,126 A | | 4/1999 | Osborn, III et al. | 604/385.1 |
| 5,938,649 A | | 8/1999 | Ducker et al. | 604/363 |
| 5,944,705 A | | 8/1999 | Ducker et al. | 604/364 |
| 5,957,906 A | | 9/1999 | Roe et al. | 604/378 |
| 5,968,025 A | | 10/1999 | Roe et al. | 604/364 |
| 6,013,063 A | | 1/2000 | Roe et al. | 604/385.1 |
| 6,025,186 A | | 2/2000 | Kirk et al. | 435/262 |
| 6,028,240 A | | 2/2000 | Wessel et al. | 604/358 |
| 6,068,899 A | | 5/2000 | Osborn, III et al. | 428/35.2 |
| 6,071,976 A | | 6/2000 | Dairoku et al. | 521/50 |
| 6,077,318 A | | 6/2000 | Trinh et al. | 8/137 |
| 6,090,399 A | * | 7/2000 | Ghosh et al. | 424/409 |
| 6,093,869 A | | 7/2000 | Roe et al. | 604/361 |
| 6,136,776 A | * | 10/2000 | Dickler et al. | 510/439 |
| 6,140,551 A | | 10/2000 | Niemeyer et al. | 604/367 |
| 6,149,934 A | | 11/2000 | Krzysik et al. | 424/443 |
| 6,150,582 A | | 11/2000 | Wada et al. | 604/372 |
| 6,153,209 A | | 11/2000 | Vega et al. | 424/404 |
| 6,156,678 A | | 12/2000 | Mukaida et al. | 442/118 |
| 6,160,198 A | | 12/2000 | Roe et al. | 604/361 |
| 6,166,285 A | | 12/2000 | Schulte et al. | 604/364 |
| 6,168,762 B1 | | 1/2001 | Reichman et al. | 422/128 |
| 6,245,361 B1 | * | 6/2001 | Merritt | 424/665 |
| 6,335,012 B1 | * | 1/2002 | Fischetti et al. | 424/94.1 |
| 6,559,189 B2 | * | 5/2003 | Baker et al. | 514/642 |

FOREIGN PATENT DOCUMENTS

| | | |
|---|---|---|
| CA | 2263473 | 2/1998 |
| CA | 2388196 | 4/2001 |
| CA | 2395678 | 7/2001 |
| JP | 62-500363 | 2/1987 |
| JP | 03-066375 | 3/1991 |
| JP | 04-269955 | 9/1992 |
| JP | 08-169860 | 7/1996 |
| JP | 11-506958 | 6/1999 |
| JP | 11-507105 | 6/1999 |
| JP | 11-263702 | 9/1999 |
| JP | 2001-508022 | 6/2001 |
| JP | 2004-529671 | 9/2004 |

OTHER PUBLICATIONS

Canadian Office Action from corresponding Canadian Patent Application No. 2,465,360 dated July 9, 2008.
Japanese Office Action from corresponding Japanese Patent Application No. 2003-541497 dated Sep. 5, 2008.

* cited by examiner

*Primary Examiner*—Tatyana Zalukaeva
*Assistant Examiner*—Lynne Anderson
(74) *Attorney, Agent, or Firm*—Ohlandt, Greeley, Ruggiero & Perle, L.L.P.

(57) ABSTRACT

There is provided a fibrous absorbent article for absorbing body fluids made up of a fibrous material defining a structure suitable for absorbing the body fluids, and disposed within the structure an effective amount, so as to reduce *Staphylococcus aureus* bacterial growth and neutralize TSS toxin-1 within the vagina, of one or more antimicrobial agents and one or more finishing agents.

8 Claims, No Drawings

CATAMENIAL DEVICE

BACKGROUND OF THE INVENTION

1. Field of the Invention

The present invention relates to absorbent products and, in particular, to absorbent products such as tampons and similar catamenial devices. More particularly, the present invention relates to tampons and other catamenial devices that reduce or inhibit the amount of bacteria within the vagina coming into contact with the catamenial device.

2. Description of the Prior Art

Menstrually occurring toxic shock syndrome (TSS), a multi-system disease associated with colonization by *Staphylococcus aureus* (*S. aureus*) bacteria, has been associated with the use of tampons during menstruation. It is believed that the disease is caused by toxic shock syndrome toxin-1 (TSST-1). This toxin has been found to have been produced by Staphylococcal strains isolated from menstrual TSS patients.

Staphylococci may be present in the vagina or in the nose or the throat or on the skin. The blood, desquamated tissue and other materials present in the vagina during menstruation are a culture medium for *S. aureus* and organisms symbiotic to Staphylococci. As the Staphylococci increase in number, toxins may be produced that are absorbed through the vaginal wall, potentially resulting in toxic shock syndrome.

There have been numerous attempts to address toxic shock syndrome through modifications to catamenial devices, and specifically, catamenial tampons.

U.S. Pat. No. 4,405,323 to Auerbach is directed to a tampon designed to eliminate the hazards of toxic shock syndrome and dysmenorrhea. The tampon has incorporated therein an antibacterial agent. The agent allegedly disperses on contact with body fluids and prevents development of the organisms that produce the toxins, which cause toxic shock syndrome. Among the antibacterial materials disclosed for use are povidone-iodine compound, mercury, zinc, penicillin, erythromycin and nitrofurazone.

Patent Cooperation Treaty Publication No. WO 86/05388 (published Sep. 25, 1986) to Kass provides that the inclusion of a salt of a nontoxic divalent cation in absorptive pads, e.g. catamenial tampons, inhibits production of toxic shock syndrome toxin-1 and other staphylococcal products during use of said absorptive pad. Suitable salts include those of magnesium, barium, calcium or strontium (preferred) or of other divalent cations such as zinc, manganese, copper, iron, nickel and the like.

In U.S. Pat. No. 4,374,522 to Olevsky, it is stated that patterns of use of catamenial tampons seem to indicate that high absorptive capacity with the concomitant extended period of use of certain tampons are factors that contribute to the formation of toxic shock syndrome. The patent provides a tampon made of conventional cellulosic materials, such as rayon fibers, which have been compressed into a bullet-shape with an open bottom surface sealed by a fluid impermeable sheet. The fluid impermeable bottom and the traditional bullet shaped pledget define a hollow core, central reservoir area, which serves as a reservoir for excess menstrual fluid.

U.S. Pat. No. 4,431,427 to Lefren et al. discloses menstrual tampons comprising physiologically safe, water-soluble acids in their monomeric, oligomeric or polymeric forms. Citric, glycolic, malic, tartaric and lactic acids are disclosed as being useful in the practice of the invention. The presence of one or more of the above-noted acids in a tampon is said to inhibit the growth of bacteria responsible for toxic shock. Where an acid is used in its polymeric form, the tampon may additionally include an enzyme to hydrolyze the polymeric acid to its monomeric form.

Canadian Patent No. 1,123,155 to Sipos discloses a catamenial tampon for preventing toxic shock syndrome during menstrual flow. The body of the tampon, which is open at the insertion end and is closed at the withdrawal end, is snugly surrounded in its expanded condition by a fluid proof, thin and flexible membrane. This membrane, which can be made of polyethylene sheet, is biased against the vaginal wall during use of the tampon, is neutral to the vaginal mucosa and is completely impermeable to bacteria, viruses and toxic decomposition products of the menstrual flow.

Canadian Patent No. 1,192,701 to Bardhan discloses a tampon for the absorption of menstrual flow. The tampon comprises an inner layer of liquid-absorbent material and an outer layer, which surrounds and encloses the inner layer. Menstrual discharge may flow inwardly to the inner layer, but the outer layer is impervious to the passage of menstrual fluid outwardly from the inner layer. A plurality of liquid absorbent wicks extending from the inner layer through apertures formed in the outer layer serve as conduits for the flow of menstrual discharge from outside the tampon to the inner layer thereof. The disclosed structure allegedly minimizes the availability of discharge outside the tampon with a resulting reduction in the likelihood of growth of *S. aureus* and consequently its production of toxin. This patent also discloses that an antimicrobial compound, which is bactericidal or bacteriostatic to *S. aureus*, may be included in the inner layer. The antimicrobial agent may take the form of an antibiotic (such as penicillin, erythromycin, tetracycline or neomycin), a chemotherapeutic agent (such as a sulfonamide) or a disinfectant (such as phenol).

U.S. Pat. No. 4,585,792 to Jacob et al. discloses that L-ascorbic acid when topically applied to the vaginal area of a human female during manses will inactivate toxins known to contribute to Toxic Shock Syndrome. The ascorbic acid compound may be carried by a vaginal tampon. The disclosure of U.S. Pat. No. 4,722,937 is to the same effect.

U.S. Pat. No. 4,413,986 to Jacobs discloses a sterilely-packaged tampon assembly for sterile insertion of a tampon into the vagina and having a guide tube telescoped around an insertion tube and a flexible sheath attached to the inner end of the guide tube and tucked into the inner end of the insertion tube. In use, as the insertion tube is pushed through the guide tube and into the vagina, the flexible sheath is pulled over the inner end of the insertion tube and extends along the exterior thereof. The portion of the insertion tube, which is inserted into the vagina, is at all times fully sheathed by the flexible sheath.

U.S. Pat. Nos. 5,389,374, 5,547,985, 5,641,503, 5,679,369, 5,705,503, and 5,753,252, all to Brown-Skrobot et al., each disclose an absorbent product having a compound for inhibiting toxins produced by *Staphylococcus aureus* bacteria. The compound is selected from the group consisting of (1) monoesters of a polyhydric aliphatic alcohol and a fatty acid containing from eight to eighteen carbon atoms, in which the monoester has at least one hydroxyl group associated with its aliphatic alcohol residue, (2) diesters of a polyhydric aliphatic alcohol and a fatty acid containing from eight to eighteen carbon atoms, in which the diester has at least one hydroxyl group associated with its aliphatic alcohol residue, and (3) mixtures of the monoesters and diesters.

SUMMARY OF THE INVENTION

It is an object of the present invention to provide an absorbent catamenial device or product, such as a tampon, that reduces or inhibits bacterial growth and toxin formation within the vagina.

It is another object of the present invention to provide a tampon that maximizes the effect of a desired amount of antibacterial agent in a tampon to reduce or inhibit bacterial growth in the vagina.

It is a further object of the present invention to provide a tampon that maximizes the effect of a desired amount of one or more finishing agents in a tampon to neutralize toxin formed in the vagina.

It is still a further object of the present invention to provide a method of incorporating the one or more antibacterial agents and the one or more finishing agents into a tampon.

The above and other objects and advantages of the present invention are fulfilled by a tampon or other similar catamenial device or product in which there is disposed an effective amount of antibacterial agent and finishing agent, capable of significantly reducing or inhibiting bacterial growth and neutralizing toxin within the vagina. Briefly stated, a broad feature of the present invention can be defined as a fibrous absorbent article for absorbing body fluids made up of a fibrous material defining a structure suitable for absorbing the body fluids, and disposed within the structure an effective amount, so as to reduce *Staphylococcus aureus* bacterial growth and neutralize TSS toxin-1 within the vagina, of one or more antimicrobial agents and one or more finishing agents.

DETAILED DESCRIPTION OF THE INVENTION

As used herein, the term "absorbent material" includes natural or synthetic fibers, nonwovens, films, foams, wood pulp, peat moss, superabsorbent polymers and the like, which are capable, either inherently or by virtue of the manner in which they have been assembled, of absorbing liquids such as water, urine, menstrual fluids, blood, and wound exudates.

As used herein, the term "absorbent products" includes catamenial tampons, wound dressings, disposable diapers, sanitary napkins, other kinds of tampons, such as those intended for medical, surgical, dental and/or nasal use, and any other article or device for absorbing body fluids therein.

In accordance with the invention, the absorbent product contains an amount of one or more antibacterial agents effective to reduce or inhibit the growth of *S. aureus* bacteria, when exposed to the absorbent product. In addition, the absorbent product has an amount of one or more finishing agents effective to neutralize TSST-1, which may have formed within the vagina when exposed to the Staphylococci.

In a preferred embodiment of the present invention, an amount of antibacterial agent and finishing agent is disposed in an absorbent product. It has been found that by disposing both the one or more antibacterial agents and the one or more finishing agents in an absorbent product, *S. aureus* bacteria growth and TSST-1 are significantly reduced as a result of the synergy between the neutralization effect of the one or more finishing agents and the bactericidal or bacteriostatic effect of the one or more antibacterial agents.

Preferably, the absorbent product is a tampon. The tampon may be made of any material known in the art to be suitable for insertion into the body and/or the absorption of body fluids. Typically, the tampon may be made of a fibrous material, such as cotton or rayon, a superabsorbent, or mixtures thereof.

Suitable antibacterial agents that may be included in the tampon, which effectively reduce *S. aureus* bacteria growth, include, without limitation, one or more quaternary ammonium compounds, glyceryl monolaurate, 5-chloro-2-(2,4-dichlorophenoxy)-2,4,4'-trichloro-2'-hydroxy diphenyl ether (triclosan), p-chloro-m-xylenol, N-(4-chlorophenyl)-N'-(3,4-dichlorophenyl) urea (triclocarban), 2-N-octyl-4-isothiazolin-3-one, iodine-based compounds, such as, for example, PVP-iodine, iodopropynyl butyl carbamate (glycacil), or diiodomethyltolylsulfone (amical), and any mixtures thereof.

It has been found that an absorbent product, such as a tampon, having one or more antibacterial agents present in an amount from about 0.01 percentage by weight (wt. %) to about 5 wt. %, based on the total weight of the tampon, is effective at significantly reducing the growth of *S. aureus* bacteria that comes into contact with the tampon.

Preferably, the one or more antibacterial agents are quaternary ammonium compounds conforming to the chemical structure:

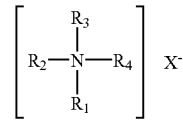

where X is selected from the group consisting of: a halogen and a saccharinate; $R_1$ and $R_3$ is a straight or branched $C_1$-$C_4$ alkyl; $R_2$ is a straight or branched $C_6$-$C_{22}$ alkyl; and $R_4$ is of the chemical structure:

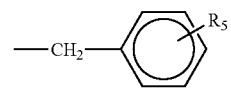

where $R_5$ is selected from the group consisting of: H, a straight or branched $C_1$-$C_4$ alkyl, and a halogen.

Preferably, the quaternary ammonium compound is, for example, alkyl dimethyl benzylammonium chloride, alkyl dimethyl ethylbenzylammonium chloride, myristyl dimethyl benzylammonium chloride, lauryl dimethyl ethylbenzylammonium chloride, alkyl dimethyl benzylammonium bromide, alkyl dimethyl benzylammonium cetyl phosphate, alkyl dimethyl benzylammonium saccharinate, or any mixtures thereof.

In a preferred embodiment of the present invention, a mixture of alkyl dimethyl benzylammonium chloride and alkyl dimethyl ethylbenzylammonium chloride, sold under the trade name BTC 2125®M by Stepan Company, is used. It is present in the tampon in an amount from about 0.01 wt. % to about 5 wt. %. More preferably, the BTC 2125®M is present in an amount from about 0.10 wt. % to about 2.5 wt. %. In the most preferred embodiment, BTC 2125®M is present in an amount from about 1.0 wt. % based on the total weight of the tampon.

Suitable finishing agents that may be included in the tampon that neutralize toxins, such as TSST-1, include, for example, one or more surfactants. Suitable surfactants that may be included in the tampon to neutralize TSST-1, may include, without limitation, one or more nonionic, anionic, cationic, amphoteric, or any mixtures thereof.

Preferably, the one or more surfactants are nonionic surfactants. Suitable nonionic surfactants may include, for example, one or more alcohol ethoxylates, alkylphenol ethoxylates, amine oxides, carboxylic acid esters, ethoxylated anhydrosorbital esters, glycerol esters, poly(oxyethylene-co-oxypropylene) based surfactants, polyoxyethylene fatty acid amines, polyoxyethylene fatty acid esters, polyethylene glycol, polyethylene glycol esters, or any mixtures thereof.

nents may be one or more preservatives, deodorants, lubricants, fragrances, malodor counteractant odor absorbing and neutralizing materials, humectants (moisturizers), or any combinations thereof.

Tampons were prepared with varying concentrations of BTC 2125®M and Tween®-20. S. aureus MN8 was incubated with these tampons, and also on tampons without antibacterial agent and surfactant. After a predetermined incubation time, the concentration of both S. aureus and TSST-1 on the tampons was measured. The results of this study are summarized in Table 1 below.

TABLE 1

Growth of S. Aureus MN8 and Production of TSST-1
When Incubated with Tampons having BTC 2125 ® M and Tween ®-20.

| APPLICATOR DESCRIPTION | AIR VOLUME (cc) | INOCULUM (cc) | FINAL pH | CFU/ml | AVERAGE | TSST-1 (ng/ml) | AVERAGE TSST-1 (ng/ml) |
|---|---|---|---|---|---|---|---|
| Tampon with 0.25% BTC and 0.25% Tween 20 | 5.7 | 8.7 | 6.65 | $3.6 \times 10^4$ | $7.7 \times 10^3$ | 200.5 | 332.28 |
| | 5.9 | 7.7 | 6.71 | $2.0 \times 10^2$ | | 159.1 | Std. = 206.29 |
| | 5.6 | 8.0 | 6.86 | <100 | | 227.8 | |
| | 5.5 | 6.9 | 6.79 | <100 | | 725.0 | |
| | 5.4 | 8.3 | 6.80 | $2.3 \times 10^3$ | 349.0 | | |
| Tampon with 0.25% BTC and 2.5% Tween 20 | 4.8 | 10.7 | 6.81 | $2.3 \times 10^5$ | $3.2 \times 10^5$ | 43.1 | 47.1 |
| | 5.4 | 12.5 | 6.82 | $5.5 \times 10^5$ | | 52.7 | Std. = 10 76 |
| | 5.3 | 10.5 | 6.82 | $1.7 \times 10^4$ | | 65.8 | |
| | 5.0 | 10.4 | 6.81 | $6\,5 \times 10^5$ | | 40.6 | |
| | 5.4 | 10.4 | 6.83 | $1.7 \times 10^5$ | | 35.1 | |
| Tampon with 1.0% BTC and 0.25% Tween 20 | 4.7 | 8.3 | 7.06 | <100 | <100 | 267.69 | 382.64 |
| | 4.9 | 7.4 | 6.96 | <100 | | 787.2 | Std. = 236.02 |
| | 5.3 | 8.6 | 6.92 | <100 | | 177.26 | |
| | 5.0 | 8.3 | 6.92 | <100 | | 507.74 | |
| | 5.0 | 8.4 | 7.04 | <100 | | 173.32 | |
| Tampon with 1.0% BTC and 2.5% Tween 20 | 5.4 | 12.9 | 7.05 | <100 | <100 | 0.97 | 17.18 |
| | 5.3 | 11.5 | 6.94 | <100 | | 30.07 | Std. = 18.23 |
| | 4.9 | 11.1 | 6.99 | <100 | | 6.12 | |
| | 5.5 | 11.6 | 7.04 | <100 | | 1.96 | |
| | 6.0 | 11.4 | 6.97 | <100 | | 46.81 | |
| Innoculum Control | 4.0 | 10.0 | 6.37 | $1.3 \times 10^9$ | $1.4 \times 10^9$ | 482.86 | 440.09 |
| | 4.0 | 10.0 | 6.38 | $1.3 \times 10^9$ | | 477.79 | Std. = 60.62 |
| | 4.0 | 10.0 | 6.39 | $1.6 \times 10^9$ | | 480.07 | |
| | 4.0 | 10.0 | 6.37 | $1.5 \times 10^9$ | | 323.88 | |
| | 4.0 | 10.0 | 6.37 | $1.4 \times 10^9$ | | 435.96 | |

Starting load of S. aureus MN8: $1.6 \times 10^6$ CFU/ml, incubated @35° C. ± 2C for 22 hours.

Suitable cationic surfactants for use in the tampon include, for example, cocamidopropyl PG dimonium chloride.

Suitable amphoteric surfactants for use in the tampon include, for example, cocamidopropyl betaine, oleamidopropyl betaines, coco-betaine, disodium cocoamphodiacetate, or any mixtures thereof.

It has been found that an absorbent product, such as a tampon, having one or more finishing agents present in an amount from about 0.01 wt. % to about 10 wt. %, based on the total weight of the tampon, is effective at significantly neutralizing toxins that come into contact with the tampon.

The preferred surfactants are a polyoxyethylene fatty acid ester, such as, for example, polysorbate-20 and an amine oxide, such as, for example, cocamidopropyl amine oxide. Most preferably, the surfactant is polysorbate-20 sold under the trade name Tween®-20. Preferably, Tween-20 is present in the tampon in an amount from about 0.01 wt. % to about 10 wt. %. More preferably, Tween®-20 is present in an amount from about 1 wt. % and about 5 wt. %. In the most preferred embodiment of the present invention, Tween®-20 is present at about 2.5 wt. % based on the total weight of the tampon.

The absorbent products of the present invention may also include one or more additional components. These compo- As demonstrated by this data, it has been found that tampons with 1.0 wt. % BTC 2125®M and 2.5 wt. % Tween®-20 significantly reduced the growth of S. aureus, as compared to the innoculum control, by greater than 7 logs from the average of $1.4 \times 10^9$ CFU/ml. The growth was reduced by greater than 4 logs from an initial bacterial load of $1.6 \times 10^6$ CFU/ml. In addition, the innoculum control average TSST-1 of 440.09 ng/ml was reduced by greater than 96% to an average of 17.18 ng/ml.

The antibacterial agent and/or the finishing agent may be incorporated in or on the surface of the absorbent article and/or fiber(s) of the present invention by any suitable process known in the art. Suitable processes may include, for example, spraying, rolling, saturating, extruding, printing, incorporating the antibacterial agent and/or finishing agent into a viscose solution prior to forming rayon fiber, applying the antibacterial agent and/or finishing agent to fibers prior to forming the absorbent article, or any combinations thereof.

Various modifications to the present invention may be made as will be apparent to those skilled in the art. Thus, it will be obvious to one of ordinary skill in the art that the foregoing description is merely illustrative of certain preferred embodiments of the present invention.

What is claimed is:

1. A tampon comprising an absorbent material and a composition disposed in said absorbent material, the composition comprising:

at least one antibacterial agent in an amount of about 0.10 wt % to about 2.5 wt % of the total weight of the tampon, wherein said antibacterial agent is a mixture of alkyl dimethyl benzylammonium chloride and alkyl dimethyl ethylbenzylammonium chloride; and at least one finishing agent in an amount of about 2.5 wt % of the total weight of the tampon, wherein said at least one finishing agent is one or more polyoxyethylene fatty acid esters, wherein the composition has synergistic antibacterial properties effective to neutralize the production of TSST-1 toxin and reduce *Staphylococcus aureus* bacteria growth.

2. The tampon of claim 1, wherein said at least one antibacterial agent is present in an amount of about 1.0 wt.% based on the total weight of the tampon.

3. The tampon of claim 1, wherein said composition further comprises one or more additional components selected from the group consisting of: preservative, deodorant, fragrance, malodor counteractant material, humectant, and any combinations thereof.

4. The tampon of claim 1, wherein said composition consists essentially of:

about 0.10 wt % to about 2.5 wt %, based on the total weight of the tampon, of a mixture of alkyl dimethyl benzylammonium chloride and alkyl dimethyl ethylbenzylammonium chloride; and about 2.5 wt %, based on the total weight of the tampon, of one or more polyoxyethylene fatty acid esters.

5. A method of inhibiting the production of TSST-1 toxin by exposing TSST-1 toxin-producing *Staphylococcus aureus* bacteria to a tampon, the tampon having an absorbent material and a composition, the composition comprising:

at least one antibacterial agent in an amount of about 0.10 wt % to about 2.5 wt % of the total weight of the tampon, wherein said antibacterial agent is a mixture of alkyl dimethyl benzylammonium chloride and alkyl dimethyl ethylbenzylammonium chloride; and at least one finishing agent in an amount of about 2.5 wt % of the total weight of the tampon, wherein said at least one finishing agent is one or more polyoxyethylene fatty acid esters;

wherein the composition has synergistic antibacterial properties effective to neutralize the production of TSST-1 toxin and reduce *Staphylococcus aureus* bacteria growth.

6. The method of claim 5, wherein said at least one antibacterial agent is present in an amount about 1.0 wt. % based on the total weight of the tampon.

7. The method of claim 5, wherein said composition further comprises one or more additional components selected from the group consisting of: preservative, deodorant, fragrance, malodor counteractant material, humectant and any combinations thereof.

8. The method of claim 5, wherein said composition consists essentially of:

about 0.10 wt % to about 2.5 wt %, based on the total weight of the tampon, of a mixture of alkyl dimethyl benzylammonium chloride and alkyl dimethyl ethylbenzylammonium chloride; and about 2.5 wt %, based on the total weight of the tampon, of one or more polyoxyethylene fatty acid esters.

* * * * *